United States Patent [19]

Kubinyi et al.

[11] Patent Number: 4,500,467
[45] Date of Patent: Feb. 19, 1985

[54] BENZOYLTHIO COMPOUNDS, THEIR PREPARATION AND THEIR USE AS DRUGS

[75] Inventors: Hugo Kubinyi, Weisenheim; Martin Traut, Heidelberg; Josef Gries, Wachenheim, all of Fed. Rep. of Germany

[73] Assignee: BASF Aktiengesellscaft, Ludwigshafen, Fed. Rep. of Germany

[21] Appl. No.: 554,098

[22] Filed: Nov. 21, 1983

[30] Foreign Application Priority Data

Nov. 24, 1982 [DE] Fed. Rep. of Germany ....... 3243370

[51] Int. Cl.³ ................. C07C 153/00; C07C 103/52; C01B 25/10
[52] U.S. Cl. ............................. 514/2; 260/112.5 R; 260/455 R; 514/19
[58] Field of Search ............... 260/455 R, 112.5 R; 424/177, 301

[56] References Cited

U.S. PATENT DOCUMENTS

| | | | |
|---|---|---|---|
| 4,127,729 | 11/1978 | Ondetti | 260/455 R |
| 4,156,785 | 5/1979 | Ondetti et al. | 260/455 R |
| 4,339,600 | 7/1982 | Ondetti et al. | 260/455 R |

OTHER PUBLICATIONS

Chem. Abstr., vol. 92, (1980), 215770.
Derwent, Abstr., J54125-669, 20.3.78.
Organic Chem. of Bivalent Sulfur, vol IV, 1962, pp. 16, 29.

Primary Examiner—Delbert R. Phillips
Attorney, Agent, or Firm—Oblon, Fisher, Spivak, McClelland & Maier

[57] ABSTRACT

Benzoylthio compounds of the formula I

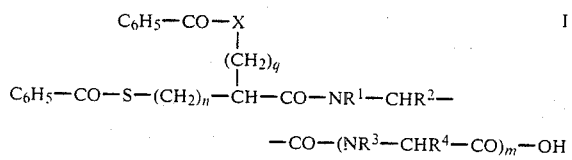

where $R^1$ and $R^3$ are identical or different and are each hydrogen or $C_1$-$C_4$-alkyl, $R^2$ and $R^4$ are identical or different and are each hydrogen or $C_1$-$C_6$-alkyl which is unsubstituted or substituted by hydroxyl, mercapto, $C_1$-$C_4$-alkylthio, a carboxylic ester group, carboxamido or acylamino or are each an aryl, hetaryl, arylalkylene or hetarylalkylene radical which is unsubstituted or substituted in the aryl moiety by hydroxyl, $C_1$-$C_4$-alkoxy, arylalkoxy or halogen, $R^1$ and $R^2$ and/or $R^3$ and $R^4$ together may furthermore be a radical $-(CH_2)_p-$ (p=2, 3, 4), $-CH_2-S-CH_2-$ or $-CH_2-C_6H_4-CH_2-$(ortho), X is NH or sulfur, m and n are identical or different and are each 0 or 1, and q is 0 or 1 where X is S, and is 0 where X is NH, and their salts with physiologically tolerated bases, their preparation, drugs containing these compounds and the use of these drugs in treating disorders.

5 Claims, No Drawings

BENZOYLTHIO COMPOUNDS, THEIR PREPARATION AND THEIR USE AS DRUGS

BACKGROUND OF THE INVENTION

1. Field of the Invention

The present invention relates to novel benzoylthio compounds, their preparation, drugs containing these compounds and the use of these drugs in treating disorders.

2. Description of the Prior Art

The renin-angiotensin system plays an important role in regulating the blood pressure of higher organisms. It is known that inhibitors of angiotension converting enzyme (ACE) lower the blood pressure and can be employed for the therapeutic treatment of high blood pressure in man. Such therapeutically useful inhibitors contain thiol, carboxyl or phosphamido groups which interact with the functional Zn atom of ACE (M. A. Ondetti and D. W. Cushman, J. Med. Chem. 24 (1981), 355 and the literature cited therein). Compounds possessing blocked thiol or carboxyl groups are, in vitro if not in vivo as well, only very weakly active or inactive (D. W. Cushman et al., Biochemistry 16 (1977), 5584, eg. compound 37; and A. A. Patchett et al., Nature 288 (1980), 280, eg. compound 10). We have found, surprisingly, that certain compounds having a blocked thiol function are very effective ACE inhibitors both in vitro and in vivo.

SUMMARY OF THE INVENTION

The present invention relates to benzoylthio compounds of the formula I

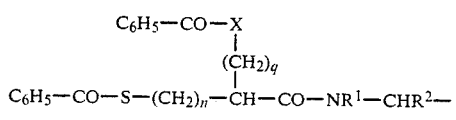

$$C_6H_5-CO-S-(CH_2)_n-CH-CO-NR^1-CHR^2-$$

$$-CO-(NR^3-CHR^4-CO)_m-OH \qquad I$$

where $R^1$ and $R^3$ are identical or different and are each hydrogen or $C_1$-$C_4$-alkyl; $R^2$ and $R^4$ are identical or different and are each hydrogen or $C_1$-$C_6$-alkyl which is unsubstituted or substituted by hydroxyl, mercapto, $C_1$-$C_4$-alkylthio, a carboxylic ester group, carboxamido or acylamino or are each an aryl, hetaryl, arylalkylene or hetarylalkylene radical which is unsubstituted or substituted in the aryl moiety by hydroxyl, $C_1$-$C_4$-alkoxy, arylalkoxy or halogen; $R^1$ and $R^2$ and/or $R^3$ and $R^4$ together may furthermore be a radical $-(CH_2)_p$-13 ($p=2$, 3, 4), $-CH_2-S-CH_2-$ or $-CH_2-C_6H_4-CH_2-$(ortho); X is NH or sulfur; m and n are identical or different and are each 0 or 1, and q is 0 or 1 where X is S, and is 0 where X is NH, and to their salts with physiologically tolerated bases.

$R^1$ is, in particular, hydrogen, but may furthermore be methyl or ethyl.

$R^2$ is, in particular, hydrogen, methyl, ethyl, propyl, isopropyl, n-butyl, isobutyl or sec.-butyl. Specific examples of substituents of these radicals are methylthio, ethylthio, methoxycarbonyl, ethoxycarbonyl, benzyloxycarbonyl, formamido, acetamido, benzamido and benzyloxycarbamido. Ring-containing substituents are, in particular, phenyl, naphthyl, thienyl, pyrrolyl, benzyl, naphthylmethylene, indolylmethylene, pyrrolylmethylene, imidazolylmethylene and thienylmethylene. $R^3$ is, in particular, hydrogen, and $R^4$ is hydrogen, $C_1$-$C_4$-alkyl, benzyl or indol-3-ylmethylene. $R^1$ and $R^2$ and/or $R^3$ and $R^4$ together may furthermore preferably be $-(CH_2)_3-$ or $-CH_2-S-CH_2-$.

DESCRIPTION OF THE PREFERRED EMBODIMENTS

Very particularly active compounds are those in which m is 0, $R^1$ is hydrogen and $R^2$ is benzyl, naphthylmethylene or indol-3-ylmethylene, or $R^1$ and $R^2$ together are $-(CH_2)_3-$ or $-CH_2-S-CH_2-$, and those in which m is 1, $R^1$ is hydrogen, $R^2$ is $C_1$-$C_4$-alkyl, and $R^3$ and $R^4$ together are $-(CH_2)_3-$ or $-CH_2-S-CH_2-$.

X is preferably sulfur and n is preferably 1.

The novel compounds are prepared by a process in which (a) an acid of the formula II

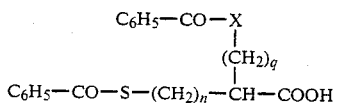

$$C_6H_5-CO-S-(CH_2)_n-CH-COOH$$

where X, n and q have the above meanings, is condensed with a compound of the formula III $$R^1NH-CHR^2-CO-(NR^3-CHR^4-CO)_m-OH \qquad III$$

where $R^1$, $R^2$, $R^3$, $R^4$ and m have the above meanings, or (b) where X is S, a compound of the formula

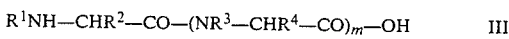

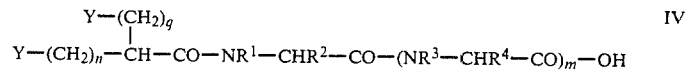

where $R^1$, $R^2$, $R^3$, $R^4$, m, n and q have the above meanings and Y is halogen, is reacted with thiobenzoic acid, and the resulting compound is, if desired, converted to its salts with physiologically tolerated bases.

For reaction by process (a), the acids (II) are converted to their carboxyl-activated derivatives. Particularly useful derivatives of this type are the acid chlorides, acid bromides, arylesters, eg. p-nitrophenyl esters, asymmetric anhydrides, eg. alkyl- or aralkylcarbonic anhydrides, N-acylazoles, eg. imidazole-N-carboxylic anhydrides, O-acyl-N,N-diacylhydroxylamines, eg. N-hydroxysuccinimide esters, and other carboxyl-activated derivatives used in peptide chemistry (Houben-Weyl, Methoden der organischen Chemie, Volume XV, Part 2, pages 2-364). To prepare the acid chlorides, the acids II are advantageously reacted with excess oxalyl dichloride in an anhydrous aprotic solvent, eg. benzene, toluene or dioxane. However, instead of oxalyl dichloride, it is also possible to use thionyl chloride, phosphorus trichloride, phosphorus pentachloride or another chlorinating agent (cf. for example Fieser and Fieser, Reagents for Organic Synthesis, Vol. I-X).

The carboxyl-activated acid derivatives are reacted directly with the compounds III. These can be used as a mixture of the D and L forms, as the D form or, preferably, as the naturally occurring L form.

The reaction is carried out in a polar aprotic organic solvent, eg. dioxane, tetrahydrofuran, ethylene glycol dimethyl ether, diethylene glycol dimethyl ether, acetonitrile, dimethylformamide or dimethyl sulfoxide, at elevated temperatures, ie. about 70°–120° C., advantageously at the boiling point of the organic solvent. The product obtained can be worked up in a conventional manner and then crystallized either directly or after purification by column chromatography, preferably over deactivated silica gel. A mixture of diastereomers of the formula I, which results from the reaction of a racemic acid of the formula II with a racemic or optically active amino acid or dipeptide of the formula III, is separated into the individual components by column chromatography or by fractional crystallization.

To prepare compounds of the formula I, it is also possible to start from the free acid of the formula II and to react this with an amino acid of the formula III whose carboxyl group is protected by an acid-labile protective group, or with a dipeptide of the formula III. A particularly suitable acid-labile protective group is tert.-butyl, but it is also possible to use other protective groups known from peptide chemistry, eg. 4-methoxybenzyl, diphenylmethyl or triphenylmethyl (cf. Houben-Weyl, Vol. XV, Part 1, pages 315–405). In this case too, the amino acids or dipeptides can be employed as a mixture of the D and L forms, as the D form or, preferably, as the naturally occurring L form. The reaction is carried out in a suitable organic solvent in the presence of a coupling reagent conventionally used in peptide chemistry, eg. dicyclohexylcarbodiimide or 1-ethyl-3-(3-dimethylaminopropyl)-carbodiimide hydrochloride (cf. Houben-Weyl, Vol. XV, Part 2, pages 103–117); where the latter coupling agent is used, the reaction may also be carried out in an organic aqueous medium.

The resulting products carrying a protective group are subjected to cleavage, either in the form of the crude product or after purification by crystallization or column chromatography, to give the compounds of the formula I. Particularly useful acids for effecting cleavage are HCl/dioxane mixtures, trifluoroacetic acid or HBr/glacial acetic acid mixtures (cf. Houben-Weyl, Vol. XV, Part I, pages 315–405).

In this case too, diastereomer mixtures can be separated into the individual components by column chromatography or by fractional crystallization. Separation can be carried out either at the stage of the carboxyl-protected derivative or at the stage of the end product.

In a preferred embodiment of the invention, where the acid of the general formula II which is used possesses an asymmetric carbon atom, this acid is employed in the form of the optically pure antipodes. To do this, either a racemate of the acid II is resolved into the antipodes with the aid of an optically active base, eg. (+)- or (−)-ephedrine, or an antipode of the acid II is prepared by benzoylating an optically active precursor.

The optical antipodes of the acid II are advantageously reacted with carboxyl-protected amino acids or dipeptides, since excessive activation of the carboxyl group of the acid II, eg. via the acid chlorides, is associated with the risk of partial or complete racemization of the acid II. In contrast, appropriately moderate activation of the carboxyl group of the acid, eg. via the N-hydroxysuccinimide ester or with a carbodiimide, does not result in any significant racemization.

Process (b) is preferably carried out using a compound of the formula IV in which Y is bromine, chlorine or iodine (Ber. 37 (1904), 2486; Fermentf. 10 (1928), 213=C. 1929 I, 2319; and J. Chem. Soc. Perkin I, 1972, 2121). This compound is reacted with thiobenzoic acid in an aprotic solvent, preferably toluene, dioxane, tetrahydrofuran, ethylene glycol dimethyl ether, acetonitrile, dimethylformamide or dimethyl sulfoxide, in the presence of an inorganic base, preferably anhydrous potassium carbonate, at from 0° to 40° C.

The acids of the formula II which are used as starting materials and in which X is —NH—, n is 0 or 1 and q is 0 are prepared by reacting an oxo acid of the general formula V

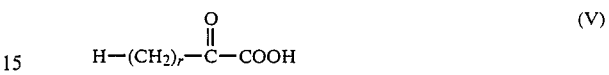

where r is 0 or 1, with benzamide and thiobenzoic acid. The reactants are employed in about equimolar amounts, and the reaction is carried out in an aprotic organic solvent, eg. benzene, toluene or dioxane, at elevated temperatures, preferably at the boiling point of the solvent, if necessary while continuously separating off the water of reaction formed. While an acid V in which r is 0 forms, as expected; an N,S-acetal, when an acid V in which r is 1 is used, an N,S-ketal is obtained as an intermediate; this undergoes cleavage and a Michael addition with thiobenzoic acid to give the desired acid II in which X is —NH—, n is 1 and q is 0.

The starting materials of the formula II in which X is sulfur are obtainable, for example, by reacting a compound of the formula VI

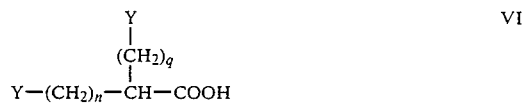

where n, q and Y have the above meanings, with thiobenzoic acid. The reaction can be carried out in the presence of potassium carbonate in acetonitrile or dioxane/water at from 0° to 40° C.

The novel compounds can be converted with a base to physiologically tolerated salts, the conversion being carried out in a conventional manner. Examples of suitable salts are ammonium salts, alkali metal salts, in particular those of sodium, potassium and lithium, alkaline earth metal salts, in particular those of calcium and magnesium, and salts with suitable organic bases, such as lower alkylamines, eg. methylamine or ethylamine, substituted lower alkylamines, in particular hydroxyl-substituted alkylamines, eg. diethanolamine, triethanolamine, tris-(hydroxymethyl)-aminomethane or diethylaminoethanol, or morpholine.

The novel compounds and their physiologically tolerated salts are useful drugs which inhibit angiotensin converting enzyme and can be used for treating hypertension.

The following method was used in investigating the pharmacodynamic effect (inhibition of angiotensin converting enzyme ex vivo in rats):

Before, and 2 hours after, oral administration of the substance, blood was withdrawn from the animals, and the plasma was diluted 1:6 with $H_2O$. The diluted plasma (100 $\mu$l) was incubated with 50 $\mu$l of $^{14}C$-hippuryl-histidylleucine solution (K phosphate 260 mM, NaCl 938 mM, pH=8.3) for 1 hour at 37° C. The reaction was terminated by adding 2 ml of 0.1N HCl, and the product, $^{14}C$-hippuric acid, was extracted with toluene scintillator (PPO+POPOP+toluene+21% of isoamyl alcohol) and determined using a scintillation counter for liquids. After subtraction of the blank value (incubation time=0 minute), the percentage inhibition was determined from the enzymatic activities in the plasma before and after administration of the substance. The ED 50%, ie. the dose which produces 50% inhibition, is calculated from the individual inhibitory values by linear regression following logit-log transformation.

The superior activity of the compounds according to the invention is evident from the Table. For example, angiotensin converting enzyme is inhibited by the substances of Examples 68 and 70 in doses which are 5 times smaller than the captopril dose.

TABLE

| Inhibiting effect on angiotensin converting enzyme | | |
|---|---|---|
| Substance of | ED 50%[1] | |
| Example | mg/kg | relative activity |
| 68 | 0.2 | 5.0 |
| 70 | 0.2 | 5.0 |
| captopril | 1.00 | 1.00 |

[1] Dose which produces 50% inhibition.

The compounds according to the invention can be administered orally or parenterally (subcutaneously, intravenously, intramuscularly or intraperitoneally) in a conventional manner, and they may furthermore be administered through the nasopharyngeal space, using vapors or sprays.

The dosage depends on the age, condition and weight of the patient and on the route of administration. As a rule, the daily dose of active compound is from about 0.1 to 10 mg/kg of body weight for oral administration, and satisfactory results are normally obtained with daily doses of from 0.2 to 2.0 mg/kg administered orally.

The novel compounds can be employed in the conventional solid or liquid pharmaceutical forms, eg. tablets, film tablets, capsules, powders, granules, coated tablets, suppositories, solutions, ointments, creams or sprays. These are prepared in a conventional manner, and to do so the active compounds can be mixed with the conventional pharmaceutical auxiliaries, such as tablet binders, fillers, preservatives, tablet disintegrators, flow regulators, plasticizers, wetting agents, dispersants, emulsifiers, solvents, retarding agents, antioxidants and/or propellants (cf. H. Sucker et al.: Pharmazeutische Technologie, Thieme Verlag, Stuttgart, 1978). The resulting forms for administration normally contain from 0.1 to 99 percent by weight of the active compound.

The Examples which follow illustrate the invention.

All melting points are uncorrected, and data on thin-layer chromatography refers to the following systems:
I=20:1 ethyl acetate/glacial acetic acid
II=10:10:1 cyclohexane/ethyl acetate/glacial acetic acid.

Thin-layer chromatography (TLC) was carried out on silica gel 60 $F_{254}$ plates from Merck, Darmstadt, with chamber saturation. The development distance was about 13 cm. In the Examples, the amino acids are the L compounds, unless D or DL is stated.

EXAMPLE 1

N-[N-Benzoyl-α-(benzoylthio)-glycyl]-glycine (a) Preparation of the starting material 9.2 g (0.1 mole) of glyoxylic acid monohydrate were refluxed together with 12.1 g (0.1 mole) of benzamide and 15.2 g (0.11 mole) of thiobenzoic acid in 200 ml of dry toluene for 3 hours. The water of reaction formed was separated off continuously via a water separator. The reaction solution was cooled and filtered, the residue was washed with toluene, and 25.4 g (81%) of N-benzoyl-α-(benzoylthio)-glycine of melting point 165°-168° C. (Rf=0.27 in system I) were obtained.

(b) Preparation of the end product 16.8 g (0.1 mole) of tert.-butyl glycine hydrochloride were suspended in 100 ml of dry acetonitrile, 10.1 g (0.1 mole) of triethylamine were added and the mixture was stirred for a short time at room temperature. A solution of 31.5 g (0.1 mole) of N-benzoyl-α-(benzoylthio)-glycine in 400 ml of dry acetonitrile and 20.6 g (0.1 mole) of dicyclohexylcarbodiimide were added to the mixture, and stirring was continued for 3 hours at room temperature. The precipitated dicyclohexylurea was filtered off, the filtrate was evaporated down under reduced pressure and the residue was taken up with ethyl acetate. The solution was filtered once again, the filtrate was evaporated down and the residue was chromatographed with 1:1 cyclohexane/ethyl acetate over a column containing deactivated silica gel. Crystallization from ethyl acetate gave 27.8 g of tert.-butyl N-[N-benzoyl-α-(benzoylthio)-glycyl]-glycine of melting point 157°-160° C. (Rf=0.50 in 1:1 cyclohexane/ethyl acetate). The product was dissolved in 100 ml of dry dioxane, 100 ml of 6N HCl/dioxane were added and the mixture was left to stand for 3 hours at 20° C. 500 ml of ethyl acetate were then added to the mixture, the organic phase was extracted by shaking with three times 500 ml of water, dried with anhydrous sodium sulfate and evaporated down under reduced pressure, and the residue was crystallized from diethyl ether. 22.8 g (61%) of N-[N-benzoyl-α-(benzoylthio)-glycyl]-glycine, melting point 194°-197° C. (Rf=0.31 in system I) were obtained.

The following compound was obtained by a similar method:

2. N-[N-Benzoyl-α-(benzoylthio)-glycyl]-alanine, in the form of a diastereomer mixture, melting point 162°-164° C. (diethyl ether), Rf=0.47 and 0.40 in system I.

EXAMPLE 3

N-[N-Benzoyl-α-(benzoylthio)-glycyl]-proline

The procedure described in Example 1b was followed, except that the addition of triethylamine was omitted and tert.-butyl proline was used instead of tert.-butyl glycine hydrochloride. In this manner, N-[N-benzoyl-α-(benzoylthio)-glycyl]-proline was obtained as an oily diastereomer mixture. Crystallization from ethyl acetate gave the non-polar isomer of melting point 202°-205° C., Rf=0.34 in system I, $[\alpha]_D^{20} = +25°$ (c=1 in chloroform). Crystallization of the mother liquors from diethyl ether/petroleum ether gave the polar isomer of melting point 182°-185° C., Rf=0.30 in system I, $[\alpha]_D^{20} = -87°$ (c=1 in chloroform).

EXAMPLE 4

N-[N-Benzoyl-α-(benzoylthio)-glycyl]-tryptophan

The procedure described in Example 1b was followed, except that the addition of triethylamine was omitted and tert.-butyl tryptophan was used instead of tert.-butyl glycine hydrochloride. To avoid side-reactions of the indole ring, ethanedithiol was added to the mixture during the acidic cleavage of the tert.-butyl ester. Crystallization from diethyl ether gave N-[N-benzoyl-α-(benzoylthio)glycyl]-tryptophan as a diastereomer mixture of melting point 188°–191° C. Separation of the mixture by chromatography with 3:2 cyclohexane/ethyl acetate over a column containing deactivated silica gel gave the non-polar isomer of melting point 180°–183° C., Rf=0.51 in system I, $[\alpha]_D^{20} = +18°$ (c=1 in 9:1 chloroform/methanol), and the polar isomer of melting point 200°–203° C., Rf=0.46 in system I, $[\alpha]_D^{20} = 0°$ (c=1 in 9:1 chloroform/methanol).

EXAMPLE 5

N-[N-Benzoyl-α-(benzoylthio)-glycyl]-alanylproline 12.1 g (50 millimoles) of tert.-butyl alanylproline (prepared by coupling benzyloxycarbonylalanine with tert.-butyl proline using dicyclohexylcarbodiimide, followed by hydrogenolytic elimination of the protective group) were dissolved in 150 ml of dry acetonitrile, a solution of 15.8 g (50 millimoles) of N-benzoyl-α-(benzoylthio)-glycine in 150 ml of dry tetrahydrofuran and 10.3 g (50 millimoles) of dicyclohexylcarbodiimide were added and the mixture was stirred overnight at room temperature. The precipitated dicyclohexylurea was filtered off under suction, and the filtrate was evaporated down under reduced pressure. The residue was chromatographed with 1:1 cyclohexane/ethyl acetate over a column containing deactivated silica gel. 20.2 g (75%) of tert.-butyl N-[N-benzoyl-α-(benzoylthio)-glycyl]-alanylproline were obtained as a diastereomer mixture. Crystallization from cyclohexane/ethyl acetate gave 7.5 g of a low-melting isomer of melting point 97°–100° C.; 7.8 g of a high-melting isomer of melting point 147°–150° C. were obtained from the mother liquor after crystallizing the product twice from cyclohexane/ethyl acetate. Cleavage of the two isomers separately, using 6N HCl/dioxane in a procedure similar to that described in Example 1b, gave N-[N-benzoyl-α-(benzoylthio)-glycyl]-alanylproline as diastereomer I (obtained in crystalline form from ethyl acetate, melting point 185°–188° C., Rf=0.18 in system I, $[\alpha]_D^{20} = +29°$ (c=1 in chloroform)) and diastereomer II (obtained in crystalline form from ethyl acetate, melting point 203°–206° C., Rf=0.18 in system I, $[\alpha]_D^{20} = -167°$ (c=1 in chloroform)).

EXAMPLE 6

N-[2,2-Bis-(benzoylthio)-acetyl]-glycine

A solution of 27.5 g (0.1 mole) of N-(2,2-dibromoacetyl)-glycine and 30.4 g (0.22 mole) of thiobenzoic acid in 100 ml of dry acetonitrile was added dropwise to a thoroughly stirred suspension of 55.3 g (0.4 mole) of anhydrous potassium carbonate in 100 ml of dry acetonitrile at from 0° to 5° C. Stirring was continued for 1 hour at from 15° to 20° C., after which the mixture was introduced into 1 liter of ice water and extracted with twice 400 ml of diethyl ether. The combined ether phases were extracted with 500 ml of 10% strength aqueous potassium carbonate solution, and the combined aqueous phases were brought to pH 3 with aqueous 2N H2SO4, while cooling. The aqueous phase was extracted with twice 400 ml of ethyl acetate, and the organic phase was dried with anhydrous sodium sulfate and evaporated down. Chromatography with 2:1 cyclohexane/ethyl acetate over a column containing deactivated silica gel gave 24.5 g (63%) of N-[2,2-bis-(benzoylthio)-acetyl]-glycine, which was obtained in crystalline form from diisopropyl ether; melting point 141°–143° C., Rf=0.50 in system I.

EXAMPLE 7

N-[2,2-Bis-(benzoylthio)-acetyl]-alanine

Preparation of the starting material (a) A solution of 43.6 g (0.2 mole) of dibromoacetic acid and 60.8 g (0.44 mole) of thiobenzoic acid in 100 ml of dry acetonitrile was added dropwise to a thoroughly stirred suspension of 110.6 g (0.8 mole) of anhydrous potassium carbonate in 150 ml of dry acetonitrile at from 0° to 5° C. Stirring was continued for a further 45 minutes at from 15° to 20° C., after which the mixture was introduced into 1 liter of ice water and was extracted with twice 400 ml of diethyl ether. The combined ether phases were extracted with 500 ml of 10% strength aqueous potassium carbonate solution, and the combined aqueous phases were brought to pH 3 with aqueous 2N H2SO4 while cooling. The aqueous phase was extracted with twice 400 ml of ethyl acetate, and the organic phases were dried with anhydrous sodium sulfate and evaporated down. The remaining oil was crystallized from benzene, the crystals were filtered off under suction and washed with benzene/petroleum ether, and 48.4 g (59%) of 2,2-bis-(benzoylthio)-acetic acid were obtained as a complex with 1 mole of benzene of crystallization; melting point 82°–83° C., Rf=0.52 in system I.

(b) 16.4 g (40 millimoles) of 2,2-bis-(benzoylthio)-acetic acid were suspended in 150 ml of toluene, and 25.4 g (0.2 mole) of oxalyl dichloride were added, while cooling. The mixture was heated at 50° C. for 2 hours, after which it was evaporated down under reduced pressure and excess oxalyl dichloride was removed by repeated co-evaporation with toluene. The remaining crude 2,2-bis-(benzoylthio)acetyl chloride could be used directly for further reactions.

Preparation of the end product 14.2 g (40 millimoles) of the crude product obtained as described in (b) were dissolved in 100 ml of dry dioxane, and the solution was added to a suspension of 3.6 g (40 millimoles) of alanine in 100 ml of dry dioxane. The reaction mixture was refluxed for 2 hours, after which the solvent was stripped off under reduced pressure. The oily crude product was chromatographed with 2:1 cyclohexane/ethyl acetate over a column containing deactivated silica gel. 10.3 g (64%) of N-[2,2-bis-(benzoylthio)-acetyl]-alanine of melting point 161°–162° C. (benzene) were obtained; Rf=0.56 in system I.

The following compounds were obtained by a similar method:

N-[2,2-bis-(benzoylthio)-acetyl]-glycine, cf. Example 6

8. N-[2,2-Bis-(benzoylthio)-acetyl]-leucine, melting point 104°–105° C. (carbon tetrachloride), Rf=0.63 in system I.

9. N-[2,2-Bis-(benzoylthio)-acetyl]-methionine, melting point 121°–122° C. (benzene/cyclohexane), Rf=0.58 in system I.

10. N-[2,2-Bis-(benzoylthio)-acetyl]-proline, melting point 80°–87° C. (after precipitation from diethyl ether/petroleum ether), Rf=0.49 in system I.

11. N-[2,2-Bis-(benzoylthio)-acetyl]-phenylalanine, melting point 161°–162° C. (benzene), Rf=0.59 in system I.

12. N-[2,2-Bis-(benzoylthio)-acetyl]-p-chlorophenylalanine, melting point 141°–142° C. (benzene), Rf=0.58 in system I.

13. D,L-2-[2,2-Bis-(benzoylthio)-acetamido]-4-phenylbutyric acid, melting point 157°–158° C. (benzene), Rf=0.60 in system I.

14. N-[2,2-Bis-(benzoylthio)-acetyl]-tryptophan, melting point from 80° C. (diethyl ether/petroleum ether), Rf=0.58 in system I.

15. N-[2,2-Bis-(benzoylthio)-acetyl]-alanylproline, melting point 199°–200° C. (ethyl acetate), Rf=0.32 in system I.

EXAMPLE 16

N-(N,S-Dibenzoyl-D,L-cysteinyl)-glycine

Preparation of starting materials (a) 264 g (3.0 moles) of freshly distilled pyruvic acid, 242.3 g (2.0 moles) of benzamide and 304.0 g (2.2 moles) of thiobenzoic acid in 2 liters of toluene were refluxed for 3 hours. The water of reaction formed and some of the excess pyruvic acid were separated off continuously via a water separator. The mixture was cooled to 70° C., and the precipitated product was filtered off and washed with warm toluene and petroleum ether to give 368.9 g (56%, based on benzamide employed) of N,S-dibenzoyl-D,L-cysteine of melting point 187°–188° C. (Rf=0.43 in system I).

(b) 63.0 g (0.4 mole) of cysteine hydrochloride were suspended in 400 ml of water, and 112.5 g (0.8 mole) of benzoyl chloride were added. A solution of 89.8 g (1.6 moles) of potassium hydroxide in 1 liter of water was added dropwise to the stirred mixture, while cooling at 0°–5° C. Stirring was continued for a further hour at room temperature, after which the mixture was rendered strongly acidic with aqueous 2N HCl, the precipitate was filtered off under suction and washed neutral with water, and the product was recrystallized twice from methanol/water. 106.3 g (81%) of N,S-dibenzoyl-cysteine of melting point 183°–185° C. were obtained; Rf=0.43 in system I, $[\alpha]_D^{20} = -85.7°$ (c=1 in absolute ethanol).

Preparation of the end product

The procedure described in Example 1b was followed, except that N,S-dibenzoyl-D,L-cysteine was used instead of N-benzoyl-α-(benzoylthio)-glycine. Owing to the poor solubility of the dibenzoylcysteine, a further 400 ml of acetonitrile and 200 ml of dry dimethylformamide were added to the reaction mixture. Working up of the mixture and elimination of the tert.-butyl group were carried out as described in Example 1b, and N-(N,S-dibenzoyl-D,L-cysteinyl)-glycine of melting point 184°–187° C. (dioxane/ethyl acetate) was obtained; Rf=0.30 in system I.

The following compounds were obtained by a procedure similar to Example 16:

17. N-(N,S-Dibenzoyl-cysteinyl)-glycine, melting point 201°–204° C. (dioxane), Rf=0.30 in system I.

18. N-(N,S-Dibenzoyl-D,L-cysteinyl)-alanine, in the form of a diastereomer mixture, melting point 160°–182° C. (diethyl ether), Rf=0.45 and 0.40 in system I.

19. N-(N,S-Dibenzoylcysteinyl)-alanine, melting point 181° C. (diethyl ether), Rf=0.44 in system I.

20. N-(N,S-Dibenzoylcysteinyl)-D-alanine, melting point 184°–185° C. (ethyl acetate/diethyl ether), Rf=0.41 in system I.

21. N-(N,S-Dibenzoyl-D,L-cysteinyl)-proline, in the form of a diastereomer mixture, melting point 85°–88° C. (petroleum ether), Rf=0.36 and 0.31 in system I.

22. N-(N,S-Dibenzoylcysteinyl)-proline, melting point 83°–86° C. (petroleum ether), Rf=0.36 in system I.

23. N-(N,S-Dibenzoylcysteinyl)-tryptophan, melting point 212°–214° C. (diethyl ether), Rf=0.19 in system II.

24. N-(N,S-Dibenzoyl-D,L-cysteinyl)-alanylproline, in the form of a diastereomer mixture, melting point 190°–193° C. (diethyl ether), Rf=0.15 in system I.

25. N-(N,S-Dibenzoylcysteinyl)-alanylproline, melting point 215°–217° C. (water), Rf=0.15 in system I.

EXAMPLE 26

N-(N,S-Dibenzoyl-D,L-cysteinyl)-tryptophan

N-(N,S-Dibenzoyl-D,L-cysteinyl)-tryptophan was obtained as a diastereomer mixture (melting point 175°–178° C., petroleum ether; Rf=0.19 and 0.16 in system II) by a procedure similar to that described in Example 16, using N,S-dibenzoyl-D,L-cysteine and tert.-butyl tryptophan as starting materials. Recrystallization from diethyl ether gave N-(N,S-dibenzoylcysteinyl)-tryptophan (melting point 210°–213° C., Rf=0.19 in system II) in a form which was pure according to thin-layer chromatography. N-(N,S-dibenzoyl-D-cysteinyl)-tryptophan (melting point 157°–160° C., Rf=0.16 in system II) which was pure according to thin-layer chromatography was obtained from the mother liquor after crystallization from petroleum ether.

EXAMPLE 27

N-[2,3-Bis-(benzoylthio)-propionyl]-glycine

Process A (a) Preparation of the starting material 115.9 g (0.5 mole) of 2,3-dibromopropionic acid and 138.2 g (1.0 mole) of thiobenzoic acid were added to a thoroughly stirred suspension, cooled to 0° C., of 276.4 g (2.0 moles) of anhydrous, powdered potassium carbonate in 700 ml of toluene. The mixture was stirred for a short time at 0° C., after which its temperature was allowed to increase slowly. At about 20° C., an exothermic reaction took place spontaneously; the reaction temperature was kept below 40° C. by cooling externally with ice water. When the reaction was complete, the mixture was diluted with 1 liter of toluene and then decanted, and the residue was digested once again with toluene and then introduced into 1 liter of ice water. After acidification with aqueous 2N H$_2$SO$_4$, the product was extracted with twice 500 ml of ethyl acetate. The organic phases were dried with anhydrous sodium sulfate and then evaporated down under reduced pressure. Crystallization from carbon tetrachloride/cyclohexane gave 117.8 g (68%) of 2,3-bis-(benzoylthio)-propionic acid of melting point 116°–118° C. (Rf=0.41 in system II).

200 g of the racemic 2,3-bis(benzoylthio)-propionic acid thus obtained were dissolved in 1.5 liters of isopropanol, and a solution of 106 g of (−)-ephedrine in 500 mL of isopropanol was added. The resulting crystals were recrystallized from methylene chloride/isopropanol, and 135.2 g of a salt of melting point 127°–129° C. and $[\alpha]_D^{20}=28.9°$ (c=1 in chloroform) were obtained. The acid was liberated by partitioning between ethyl acetate and 10% strength aqueous potassium bisulfate solution by shaking, the organic phase was evaporated down, the residue was crystallized from diethyl ether/petroleum ether, and a mixture of the racemate and the (R) form was initially obtained; the mother liquor then gave 33.7 g of (R)-2,3-bis-(benzoylthio)-propionic acid of melting point 95°–96° C., $[\alpha]_D^{20} = -99°$ (c = 1 in chloroform). The acid was liberated from the mother liquor obtained in the crystallization of the (−)-ephedrine salt, and a salt with (+)-ephedrine was formed. 97.8 g of this salt of melting point 127°–129° C., $[\alpha]_D^{20} = +33.9°$ (c = 1 in chloroform), were obtained. Cleavage of the salt and crystallization from diethyl ether/petroleum ether initially gave a mixture of the racemate and the (S) form; the mother liquor then gave 26.6 g of (S)-2,3-bis-(benzoylthio)-propionic acid of melting point 95°–96° C., $[\alpha]_D^{20} = +103°$ (c = 1 in chloroform). In addition to the two antipodes, a total of 122.4 g of racemic 2,3-bis-(benzoylthio)-propionic acid was recovered, and this can be reused in a resolution of the racemate.

Using a procedure similar to that described in Example 7b, the racemic acid was converted to the acid chloride. This can be used directly for further reactions.

(b) Preparation of the end product 18.4 g (50 millimoles) of the racemic acid chloride obtained as described in (a) were dissolved in 100 ml of dry dioxane, and the solution was added to a suspension of 3.8 g (50 millimoles) of glycine in 100 ml of dry dioxane. The reaction mixture was refluxed for 2 hours, after which the solvent was stripped off under reduced pressure. Crystallization of the residue from ethyl acetate gave 9.3 g (46%) of N-[2,3-bis-(benzoylthio)-propionyl]-glycine of melting point 160°–163° C., Rf=0.59 in system I. Chromatography of the mother liquor with 1:1 cyclohexane/ethyl acetate over a column containing deactivated silica gel gave further product which was pure according to thin-layer chromatography (melting point 162°–164° C.).

Process B

A solution of 30.1 g (0.1 mole) of N-(2,3-dibromopropionyl)-glycine and 30.4 g (0.22 mole) of thiobenzoic acid in 100 ml of dry acetonitrile was added dropwise to a thoroughly stirred suspension of 55.3 g (0.4 mole) of anhydrous potassium carbonate in 100 ml of dry acetonitrile at from 0° to 5° C. Stirring was continued for 1 hour at 20° C., after which the mixture was introduced into 1 liter of ice water and extracted with twice 400 ml of diethyl ether. The combined ether phases were extracted with 500 ml of 10% strength aqueous potassium carbonate solution, and the combined aqueous phases were brought to pH 3 with aqueous 2N $H_2SO_4$, while cooling. The aqueous phase was extracted with twice 400 ml of ethyl acetate, and the organic phase was dried with anhydrous sodium sulfate and evaporated down. Chromatography with 1:1 cyclohexane/ethyl acetate over a column containing deactivated silica gel gave 25.4 g (63%) of N-[2,3-bis-(benzoylthio)-propionyl]-glycine of melting point 162°–164° C. (ethyl acetate).

The following compounds were obtained by a procedure similar to that described in Example 27 (the crude products were purified by chromatography with from 3:1 to 1:1 cyclohexane/ethyl acetate over a column containing deactivated silica gel):

28. N-[2,3-Bis-(benzoylthio)-propionyl]-sarcosine, Rf=0.58 in system I.

29. N-[2,3-Bis-(benzoylthio)-propionyl]-alanine, melting point 152°–155° C. (cyclohexane/ethyl acetate), Rf=0.32 in system II.

30. N-[2,3-Bis-(benzoylthio)-propionyl]-D,L-norleucine, in the form of a diastereomer mixture, melting point 126°–127° C. (diethyl ether), Rf=0.39 in system II.

31. N-[2,3-Bis-(benzoylthio)-propionyl]-leucine, in the form of a diastereomer mixture, melting point 90°–93° C. (cyclohexane/ethyl acetate), Rf=0.38 in system II.

32. N-[2,3-Bis-(benzoylthio)-propionyl]-threonine, in the form of a diastereomer mixture, melting point 156°–159° C. (diethyl ether), Rf=0.44 and 0.40 in system I.

33. N-[2,3-Bis-(benzoylthio)-propionyl]-cysteine, in the form of a diastereomer mixture, melting point 171°–173° C. (ethyl acetate), Rf=0.34 in system II.

34. N-[2,3-Bis-(benzoylthio)-propionyl]-L-penicillamine, in the form of a diastereomer mixture, melting point 114°–117° C. (diisopropyl ether), Rf=0.43 in system II.

35. N-[2,3-Bis-(benzoylthio)-propionyl]-methionine, in the form of a diastereomer mixture, melting point 124°–127° C. (cyclohexane/ethyl acetate); Rf=0.38 in system II.

36. γ-Benzyl N-[2,3-bis-(benzoylthio)-propionyl]-glutamate, in the form of a diastereomer mixture, melting point 93°–96° C. (diethyl ether/petroleum ether), Rf=0.36 in system II.

37. Nα-[2,3-Bis-(benzoylthio)-propionyl]-glutamine, in the form of a diastereomer mixture, Rf=0.48 in system I.

38. Nα-[2,3-Bis-(benzoylthio)-propionyl]-Nε-(benzyloxycarbonyl)-lysine, in the form of a diastereomer mixture, melting point 107°–110° C. (diethyl ether), Rf=0.64 in system I.

39. N-[2,3-Bis-(benzoylthio)-propionyl]-D,L-azetidine-2-carboxylic acid, in the form of a diastereomer mixture, Rf=0.41 and 0.37 in system I.

40. N-[2,3-Bis-(benzoylthio)-propionyl]-D,L-piperidine-2-carboxylic acid, in the form of a diastereomer mixture, melting point 162°–165° C., Rf=0.66 in system I.

41. N-[2,3-Bis-(benzoylthio)-propionyl]-D,L-1,2,3,4-tetrahydroisoquinoline-3-carboxylic acid, in the form of a diastereomer mixture, Rf=0.67 in system I.

42. N-[2,3-Bis-(benzoylthio)-propionyl]-D,L-α-phenylglycine, in the form of a diastereomer mixture, melting point 169°–179° C. (diethyl ether), Rf=0.37 in system II.

43. N-[2,3-Bis-(benzoylthio)-propionyl]-D,L-α-(thien-3-yl)-glycine, in the form of a diastereomer mixture, melting point 161°–164° C. (diethyl ether), Rf=0.35 in system II.

44. N-[2,3-Bis-(benzoylthio)-propionyl]-phenylalanine, in the form of a diastereomer mixture, melting point 104°–107° C. (toluene/petroleum ether), Rf=0.39 in system II.

45. N-[2,3-Bis-(benzoylthio)-propionyl]-tyrosine, in the form of a diastereomer mixture, Rf=0.27 in system II.

46. N-[2,3-Bis-(benzoylthio)-propionyl]-D,L-(3,4-dimethoxy)-phenylalanine, in the form of a diastereomer mixture, Rf=0.25 in system II.

47. N-[2,3-Bis-(benzoylthio)-propionyl]-O-benzyltyrosine, in the form of a diastereomer mixture, melting point 173°–176° C. (ethyl acetate/petroleum ether), Rf=0.38 in system II.

48. N-[2,3-Bis-(benzoylthio)-propionyl]-p-chlorophenylalanine, in the form of a diastereomer mixture, Rf=0.37 in system II.

49. N-[2,3-Bis-(benzoylthio)-propionyl]-D,L-3-(naphth-1-yl)-alanine, in the form of a diastereomer mixture, Rf=0.37 in system II.

50. N-[2,3-Bis-(benzoylthio)-propionyl]-D,L-3-(naphth-2-yl)-alanine, in the form of a diastereomer mixture, melting point 140°–143° C. (cyclohexane/ethyl acetate), Rf=0.36 in system II.

51. D,L-2-[2,3-Bis-(benzoylthio)-propionamido]-4-phenylbutyric acid, in the form of a diastereomer mixture, melting point 157°–160° C. (ethyl acetate/petroleum ether), Rf=0.38 in system II.

52. N-[2,3-Bis-(benzoylthio)-propionyl]-tryptophan, in the form of a diastereomer mixture, melting point 180°–183° C. (ethyl acetate), Rf=0.34 in system II.

53. N-[2,3-Bis-(benzoylthio)-propionyl]-D-tryptophan, in the form of a diastereomer mixture, melting point 182°–185° C. (ethyl acetate), Rf=0.34 in system II.

54. N-[2,3-Bis-(benzoylthio)-propionyl]-N-methyltryptophan, in the form of a diastereomer mixture, Rf=0.35 in system II.

55. N-[2,3-Bis-(benzoylthio)-propionyl]-prolylproline, in the form of a diastereomer mixture, Rf=0.22 in system I.

56. N-[2,3-Bis-(benzoylthio)-propionyl]-phenylalanylalanine, in the form of a diastereomer mixture, melting point 110°–113° C. (diethyl ether), Rf=0.62 in system I.

57. N-[2,3-Bis-(benzoylthio)-propionyl]-tryptophylproline, in the form of a diastereomer mixture, Rf=0.62 in system I.

EXAMPLE 58

N-[2,3-Bis-(benzoylthio)-propionyl]-serine

The procedure described in Example 27 was followed, except that serine was used instead of glycine. Chromatography with 1:1 cyclohexane/ethyl acetate over a column containing deactivated silica gel gave N-[2,3-bis-(benzoylthio)-propionyl]-serine in the form of a diastereomer mixture. Fractional crystallization from ethyl acetate gave the diastereomers N-[(R)-2,3-bis-(benzoylthio)-propionyl]-serine, melting point 184°–187° C., Rf=0.35 in system I, $[\alpha]_D^{20} = -60°$ (c=1 in 9:1 chloroform/methanol), and N-[(S)-2,3-bis-(benzoylthio)-propionyl]-serine, melting point 147°–150° C., Rf=0.39 in system I, $[\alpha]_D^{20} = +116°$ (c=1 in 9:1 chloroform/methanol).

EXAMPLE 59

N-[2,3-Bis-(benzoylthio)-propionyl]-valine

The procedure described in Example 27 was followed, except that valine was used instead of glycine. Column chromatography with 3:1 cyclohexane/ethyl acetate over a column containing deactivated silica gel gave N-[2,3-bis-(benzoylthio)-propionyl]-valine in the form of a diastereomer mixture. Fractional crystallization from diethyl ether and diethyl ether/petroleum ether gave the diastereomers N-[(S)-2,3-bis-(benzoylthio)-propionyl]-valine, melting point 157°–160° C., Rf=0.39 in system II, $[\alpha]_D^{20} = +152°$ (c=1 in chloroform), and N-[(R)-2,3-bis-(benzoylthio)-propionyl]-valine, melting point 83°–90° C., Rf=0.37 in system II, $[\alpha]_D^{20} = -69°$ (c=1 in chloroform).

EXAMPLE 60

N-[2,3-Bis-(benzoylthio)-propionyl]-isoleucine

The procedure described in Example 27 was followed, except that isoleucine was used instead of glycine. Column chromatography with 3:1 cyclohexane/ethyl acetate over a column containing deactivated silica gel gave N-[2,3-bis-(benzoylthio)-propionyl]-isoleucine in the form of a diastereomer mixture. Fractional crystallization from diethyl ether and diisopropyl ether gave the diastereomers N-[(S)-2,3-bis-(benzoylthio)-propionyl]-isoleucine, melting point 151°–153° C., Rf=0.39 in system II, $[\alpha]_D^{20} = +135°$ (c=1 in chloroform), and N-[(R)-2,3-bis-(benzoylthio)-propionyl]-isoleucine, melting point 94°–95° C., Rf=0.39 in system II, $[\alpha]_D^{20} = -65°$ (c=1 in chloroform).

EXAMPLE 61

N-[2,3-Bis-(benzoylthio)-propionyl]-L-thiazolidine-4-carboxylic acid

The procedure described in Example 27 was followed, except that L-thiazolidine-4-carboxylic acid was used instead of glycine. Chromatography with 2:1 cyclohexane/ethyl acetate over a column containing deactivated silica gel gave the two diastereomers N-[(S)-2,3-bis-(benzoylthio)-propionyl]-L-thiazolidine-4-carboxylic acid, melting point 133°–138° C. (diethyl ether), Rf=0.61 in system I, $[\alpha]_D^{20} = +82°$ (c=1 in chloroform), and N-[(R)-2,3-bis-(benzoylthio)-propionyl]-L-thiazolidine-4-carboxylic acid, Rf=0.57 in system I, $[\alpha]_D^{20} = -145°$ (c=1 in chloroform).

The following compounds were obtained by a similar method:

62. N-[(R)-2,3-Bis-(benzoylthio)-propionyl]-prolylphenylalanine, Rf=0.50 in system I, $[\alpha]_D^{20} = -133°$ (c=1 in chloroform).

63. N-[(S)-2,3-Bis-(benzoylthio)-propionyl]-prolylphenylalanine, Rf=0.45 in system I, $[\alpha]_D^{20} = +41°$ (c=1 in chloroform).

EXAMPLE 64

N-[2,3-Bis-(benzoylthio)-propionyl]-alanylproline

The procedure described in Example 27 was followed, except that alanylproline was used instead of glycine. The reaction product crystallized directly from the reaction mixture. Recrystallization from isopropanol gave N-[2,3-bis-(benzoylthio)-propionyl]-alanylproline in the form of a diastereomer mixture, melting point 185°–186° C., Rf=0.40 in system I, $[\alpha]_D^{20} = -39°$ (c=1 in chloroform). Fractional crystallization of the mixture from ethyl acetate and ethyl acetate/diethyl ether gave the following diastereomers: N-[(R)-2,3-bis-(benzoylthio)-propionyl]-alanylproline, melting point 196°–197° C., Rf=0.40 in system I, $[\alpha]_D^{20} = -122°$ (c=1 in chloroform), and N-[(S)-2,3-bis-(benzoylthio)-propionyl]-alanylproline, melting point 172°–173° C., Rf=0.40 in system I, $[\alpha]_D^{20} = +36°$ (c=1 in chloroform).

EXAMPLE 65

N-[(S)-2,3-Bis-(benzoylthio)-propionyl]-proline

A solution of 8.7 g (25 millimoles) of (S)-2,3-bis-(benzoylthio)-propionic acid and 4.8 g (25 millimoles) of 1-ethyl-3-(3-dimethylaminopropyl)-carbodiimide hydrochloride in 125 ml of a 4:1 mixture of tetrahydrofuran and water was added to 4.4 g (25 millimoles) of tert.-butyl proline (crude product, obtained by hydrogenation of 7.6 g of tert.-butyl Z-proline) in 100 ml of tetrahydrofuran, while cooling at 0° C. The mixture was stirred for 1 hour at 0° C. and then for 1 hour at 20° C., after which it was partitioned between ethyl acetate and water by shaking, and the organic phase was dried with anhydrous sodium sulfate and evaporated down under reduced pressure. Chromatography with 2:1 cyclohexane/ethyl acetate over a column containing deactivated silica gel gave 9.0 g (72%) of tert.-butyl N-[(S)-2,3-bis-(benzoylthio)-propionyl]-proline. The crude product was dissolved in 50 ml of dry dioxane, 50 ml of 6N HCl/dioxane were added and the mixture was left to stand for 1 hour at 20° C. It was partitioned between ethyl acetate and water by shaking, the organic phase was washed twice with water, dried with anhydrous sodium sulfate and evaporated down under reduced pressure and 7.8 g (70%) of N-[(S)-2,3-bis-(benzoylthio)-propionyl]-proline, melting point 155°–158° C. (cyclohexane/ethyl acetate), Rf=0.56 in system I, $[\alpha]_D^{20} = +76°$ (c=1 in chloroform), were obtained.

The following compounds were obtained by a procedure similar to that described in Example 65 (the crude products were purified by chromatography with from 3:1 to 1:1 cyclohexane/ethyl acetate over a column containing deactivated silica gel):

66. N-[(R)-2,3-Bis-(benzoylthio)-propionyl]-proline, Rf=0.54 in system I, $[\alpha]_D^{20} = -117°$ (c=1 in chloroform).

67. N-[(S)-2,3-Bis-(benzoylthio)-propionyl]-tryptophan, Rf=0.34 in system II, $[\alpha]_D^{20} = +84°$ (c=1 in chloroform).

68. N-[(R)-2,3-Bis-(benzoylthio)-propionyl]-tryptophan, Rf=0.34 in system II, $[\alpha]_D^{20} = -77°$ (c=1 in chloroform).

69. N-[(S)-2,3-Bis-(benzoylthio)-propionyl]-alanyl-proline, melting point 175°–176° C. (ethyl acetate), Rf=0.40 in system I, $[\alpha]_D^{20} = +36°$ (c=1 in chloroform).

70. N-[(R)-2,3-Bis-(benzoylthio)-propionyl]-alanyl-proline, melting point 195°–196° C. (ethyl acetate), Rf=0.40 in system I, $[\alpha]_D^{20} = -125°$ (c=1 in chloroform).

EXAMPLE 71

N-[(S)-2,3-Bis-(benzoylthio)-propionyl]-valylproline

The procedure described in Example 61 was followed, except that N-[(S)-2,3-bis-(benzoylthio)-propionyl]-valine (Example 59) was used instead of (S)-2,3-bis-(benzoylthio)-propionic acid. Chromatography with 1:1 cyclohexane/ethyl acetate over a column containing deactivated silica gel gave N-[(S)-2,3-bis-(benzoylthio)-propionyl]-valylproline, melting point 85°–93° C. (diethyl ether/pentane), Rf=0.54 in system I, $[\alpha]_D^{20} = +53°$ (c=1 in chloroform).

The following compounds are prepared by a procedure similar to that described in Example 71:

72. N-[(R)-2,3-Bis-(benzoylthio)-propionyl]-valylproline, melting point 97°–100° C. (diethyl ether), Rf=0.54 in system I, $[\alpha]_D^{20} = -114°$ (c=1 in chloroform).

73. N-[(S)-2,3-Bis-(benzoylthio)-propionyl]-valyl-tryptophan, melting point 173°–181° C. (toluene), Rf=0.60 in system I.

74. N-[(R)-2,3-Bis-(benzoylthio)-propionyl]-valyl-tryptophan, melting point 205°–208° C. (toluene), Rf=0.60 in system I.

EXAMPLE 75

N-[3,3'-Bis-(benzoylthio)-isobutyryl]-glycine (a) Preparation of the starting material 14.5 g (105 millimoles) of thiobenzoic acid were added dropwise to a stirred solution of 10.6 g (50 millimoles) of 2-iodomethylacrylic acid and 13.8 g (100 millimoles) of potassium carbonate in 100 ml of a 2:3 mixture of dioxane and water. The mixture was stirred for 3 hours at room temperature, after which it was diluted with 500 ml of water, brought to pH 3 with aqueous 1N sulfuric acid and extracted by shaking with twice 300 ml of ethyl acetate. The combined organic phases were washed with a little water, dried with anhydrous sodium sulfate and evaporated down under reduced pressure. Crystallization of the residue from cyclohexane gave 15.5 g (86%) of 3,3'-bis-(benzoylthio)-isobutyric acid of melting point 107°–109° C. (Rf=0.45 in system II).

(b) Preparation of the end product 14.4 g (40 millimoles) of 3,3'-bis-(benzoylthio)-isobutyric acid were suspended in 120 ml of toluene, and 25.4 g (200 millimoles) of oxalyl dichloride were added, while cooling. The mixture was heated at 50° C. for 2 hours, after which it was evaporated down under reduced pressure and excess oxalyl dichloride was removed by repeated co-evaporation with toluene.

The residue was taken up in 150 ml of dry dioxane, and the solution was refluxed for 2 hours together with 3.0 g (40 millimoles) of glycine. The mixture was then evaporated down under reduced pressure. Chromatography with 2:1 cyclohexane/ethyl acetate over a column containing deactivated silica gel gave 12.7 g (76%) of N-[3,3'-bis-(benzoylthio)-isobutyryl]-glycine of melting point 113°–114° C. (diethyl ether), Rf=0.58 in system I.

The following compounds were obtained by a similar procedure (the crude products were purified by chromatography with from 3:1 to 1:1 cyclohexane/ethyl acetate over a column containing deactivated silica gel):

76. N-[3,3'-Bis-(benzoylthio)-isobutyryl]-sarcosine, melting point 130°–132° C. (diethyl ether/petroleum ether), Rf=0.59 in system I.

77. N-[3,3'-Bis-(benzoylthio)-isobutyryl]-alanine, melting point 145°–146° C. (diethyl ether), Rf=0.31 in system II.

78. N-[3,3'-Bis-(benzoylthio)-isobutyryl]-D-alanine, melting point 144°–145° C. (diethyl ether), Rf=0.31 in system II.

79. N-[3,3'-Bis-(benzoylthio)-isobutyryl]-D,L-norleucine, melting point 132°–133° C. (diethyl ether/petroleum ether), Rf=0.39 in system II.

80. N-[3,3'-Bis-(benzoylthio)-isobutyryl]-valine, Rf=0.38 in system II.

81. N-[3,3'-Bis-(benzoylthio)-isobutyryl]-isoleucine, Rf=0.38 in system II.

82. N-[3,3'-Bis-(benzoylthio)-isobutyryl]-leucine, melting point 93°–94° C. (diethyl ether/petroleum ether), Rf=0.37 in system II.

83. N-[3,3'-Bis-(benzoylthio)-isobutyryl]-methionine, melting point 113°–114° C. (diethyl ether/petroleum ether), Rf=0.36 in system II.

84. N-[3,3'-Bis-(benzoylthio)-isobutyryl]-serine, Rf=0.38 in system I.

85. N-[3,3'-Bis-(benzoylthio)-isobutyryl]-cysteine, Rf=0.35 in system II.

86. N-[3,3'-Bis-(benzoylthio)-isobutyryl]-proline, melting point 137°–138° C. (ethyl acetate), Rf=0.56 in system I.

87. N-[3,3'-Bis-(benzoylthio)-isobutyryl]-D-proline, melting point 136°–138° C. (ethyl acetate), Rf=0.56 in system I.

88. N-[3,3'-Bis-(benzoylthio)-isobutyryl]-thiazolidine-4-carboxylic acid, melting point 127°–129° C. (diethyl ether), Rf=0.60 in system I.

89. N-[3,3'-Bis-(benzoylthio)-isobutyryl]-D,L-azetidine-2-carboxylic acid, Rf=0.43 in system I.

90. N-[3,3'-Bis-(benzoylthio)-isobutyryl]-D,L-piperidine-2-carboxylic acid, Rf=0.67 in system I.

91. N-[3,3'-Bis-(benzoylthio)-isobutyryl]-D,L-1,2,3,4-tetrahydroisoquinoline-3-carboxylic acid, Rf=0.66 in system I.

92. N-[3,3'-Bis-(benzoylthio)-isobutyryl]-D,L-α-phenylglycine, melting point 158°–160° C. (diethyl ether/petroleum ether), Rf=0.37 in system II.

93. N-[3,3'-Bis-(benzoylthio)-isobutyryl]-phenylalanine, melting point 57°–60° C. (diethyl ether/petroleum ether), Rf=0.39 in system II.

94. N-[3,3'-Bis-(benzoylthio)-isobutyryl]-D-phenylalanine, melting point 59°–61° C. (diethyl ether/petroleum ether), Rf=0.39 in system II.

95. N-[3,3'-Bis-(benzoylthio)-isobutyryl]-tyrosine, melting point 71°–73° C. (petroleum ether), Rf=0.27 in system II.

96. N-[3,3'-Bis-(benzoylthio)-isobutyryl]-D,L-(3,4-dimethoxy)-phenylalanine, melting point 159°–161° C. (ethyl acetate), Rf=0.25 in system II.

97. N-[3,3'-Bis-(benzoylthio)-isobutyryl]-O-benzyltyrosine, Rf=0.36 in system II.

98. N-[3,3'-Bis-(benzoylthio)-isobutyryl]-p-chlorophenylalanine, melting point 143°–146° C. (diethyl ether), Rf=0.35 in system II.

99. N-[3,3'-Bis-(benzoylthio)-isobutyryl]-D,L-3-(naphth-1-yl)-alanine, Rf=0.37 in system II.

100. N-[3,3'-Bis-(benzoylthio)-isobutyryl]-D,L-3-(naphth-2-yl)-alanine, Rf=0.37 in system II.

101. D,L-2-[3,3'-Bis-(benzoylthio)-isobutyramido]-4-phenylbutyric acid, melting point 135°–136° C. (diethyl ether/cyclohexane), Rf=0.38 in system II.

102. N-[3,3'-Bis-(benzoylthio)-isobutyryl]-tryptophan, melting point 135°–139° C. (diethyl ether/petroleum ether), Rf=0.35 in system II.

103. N-[3,3'-Bis-(benzoylthio)-isobutyryl]-D-tryptophan, melting point 137°–140° C. (diethyl ether/petroleum ether), Rf=0.35 in system II.

104. N-[3,3'-Bis-(benzoylthio)-isobutyryl]-N-methyl-tryptophan, Rf=0.37 in system II.

105. N-[3,3'-Bis-(benzoylthio)-isobutyryl]-alanylproline, melting point from 60° C. (methylene chloride/petroleum ether), Rf=0.39 in system I.

106. N-[3,3'-Bis-(benzoylthio)-isobutyryl]-prolylphenylalanine, melting point 134°–135° C. (diethyl ether), Rf=0.47 in system I.

107. N-[3,3'-Bis-(benzoylthio)-isobutyryl]-prolylproline, Rf=0.23 in system I.

108. N-[3,3'-Bis-(benzoylthio)-isobutyryl]-phenylalanylalanine, Rf=0.62 in system I.

109. N-[3,3'-Bis-(benzoylthio)-isobutyryl]-valylproline, Rf=0.54 in system I.

110. N-[3,3'-Bis-(benzoylthio)-isobutyryl]-valyltryptophan, Rf=0.58 in system I.

EXAMPLE A

A mixture of the following composition is pressed on a tableting press in a conventional manner to give tablets:
40 mg of the substance of Example 62
120 mg of corn starch
13.50 mg of gelatin
45 mg of lactose
22.5 mg of talc
2.25 mg of Aerosil ® (chemically pure silica in the form of submicroscopic particles)
6.75 mg of potato starch (as a 6% strength paste)

EXAMPLE B

Coated tablets having the following composition are prepared in a conventional manner:
20 mg of the substance of Example 62
60 mg of core material
60 mg of sugar-coating material
The core material consists of 9 parts of corn starch, 3 parts of lactose and 1 part of Luviskol ® VA 64 (60:40 vinylpyrrolidone/vinyl acetate copolymer, cf. Pharm. Ind. 1962, 586). The sugar-coating material consists of 5 parts of sucrose, 2 parts of corn starch, 2 parts of calcium carbonate and 1 part of talc.

We claim:

1. An angiotensin converting enzyme inhibitor which is selected from the group consisting of benzoylthio compounds of the formula

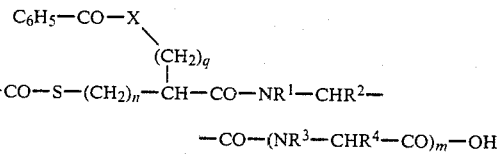

wherein
$R^1$ and $R^3$ are identical or different and are each hydrogen or $C_1$–$C_4$ alkyl;
$R^2$ and $R^4$ are identical or different and are each hydrogen;
$C_1$–$C_6$ alkyl which is unsubstituted or substituted by hydroxyl, mercapto, $C_1$–$C_4$ alkylthio, a carboxylic ester group, carboxamido, or acylamino;
aryl;
hetaryl;
arylakylene; or
hetarylalkylene radical which is unsubstituted or substituted in the aryl moiety by hydroxyl, $C_1$–$C_4$ alkoxy, arylalkoxy, or halogen; with the proviso that $R^1$ and $R^4$ together or $R^3$ and $R^4$ together may furthermore be a radical selected from
—$(CH_2)_p$—, wherein p is 2–4,
—$CH_2$—S—$CH_2$—, or
ortho—$CH_2$—$C_6H_4$—$CH_2$—;
X is NH or sulfur;
m and n are identical or different and are each 0 or 1; and
q is 0;
or a salt of said inhibitor with a physiologically acceptable base.

2. The inhibitor of claim 1, wherein
$R^1$ and $R^3$ are each hydrogen;
$R^2$ is hydrogen, $C_1$–$C_4$ alkyl, benzyl, naphthylmethylene, or indol-3-ylmethylene;
$R^4$ is $C_1$–$C_4$ alkyl, benzyl, or indol-3-ylmethylene;

with the proviso that $R^1$ and $R^2$ together or $R^3$ and $R^4$ together may furthermore be —(CH$_2$)$_3$— or —CH$_2$—S—CH$_2$—;

X is sulfur; and n and m are identical or different and are each 0 or 1, and q is 0, or a salt of said inhibitor with a physiologically acceptable base.

3. The inhibitor of claim 1 wherein $R^4$ is hydrogen, $C_1$-$C_4$ alkyl, benzyl or indol-3-ylmethylene, and $R^2$ is an alkyl group selected from the group consisting of methyl, ethyl, propyl, isopropyl, n-butyl, isobutyl, and sec-butyl; said alkyl group being optionally substituted with a substituent selected from the group consisting of methylthio, ethylthio, methoxycarbonyl, ethoxycarbonyl, benzyloxycarbonyl, formamido, acetamido, benzamido, and benzyloxycarbamido; or $R^2$ is an aryl, hetaryl, alkylalkylene or an hetarylalkylene group selected from the group consisting of phenyl, naphthyl, thienyl, pyrrolyl, benzyl, naphthylmethylene, indolylmethylene, pyrrolylmethylene, imidazoylmethylene, and thienylmethylene.

4. A therapeutic composition comprising a pharmaceutical excipient and an antihypertension effective amount of a benzoylthio compound according to claim 1 as the active compound.

5. The method of treating hypertension in a patient suffering therefrom, which comprises administering an effective amount of a benzoylthio compound according to claim 1.

* * * * *